United States Patent [19]
Allen

[11] Patent Number: 5,730,155
[45] Date of Patent: Mar. 24, 1998

[54] ETHMOIDAL IMPLANT AND EYEGLASS ASSEMBLY AND ITS METHOD OF LOCATION IN SITU

[76] Inventor: Dillis V. Allen, 31W211 Rte. 58, Elgin, Ill. 60120

[21] Appl. No.: 410,971

[22] Filed: Mar. 27, 1995

[51] Int. Cl.$^6$ .................................................. A61B 19/00
[52] U.S. Cl. ........................................... 128/897; 351/41
[58] Field of Search ............... 128/897–99; 623/4–6; 351/41, 65, 103, 110

[56] References Cited

U.S. PATENT DOCUMENTS

| | | |
|---|---|---|
| 78,534 | 6/1868 | Moses . |
| 5,060,635 | 10/1991 | Steur et al. . |
| 5,167,961 | 12/1992 | Lussi et al. . |
| 5,198,308 | 3/1993 | Shetty et al. . |
| 5,220,918 | 6/1993 | Heide et al. . |
| 5,259,398 | 11/1993 | Vrespa . |

*Primary Examiner*—Lee S. Cohen
*Assistant Examiner*—John Lacyk

[57] ABSTRACT

An ocular ethmoidal implant and eyeglass assembly including a titanium screw implant adapted to be threaded in situ into the ethmoidal area horizontally, a pair of subcutaneous magnet assemblies threaded into the ends of the implant contoured to the proximal ethmoidal surface, and a non-implant engaging or contacting eyeglass assembly with nosepiece carried magnets supracutaneously positioned over and held in position and oriented about three axes by the implant magnets.

16 Claims, 3 Drawing Sheets

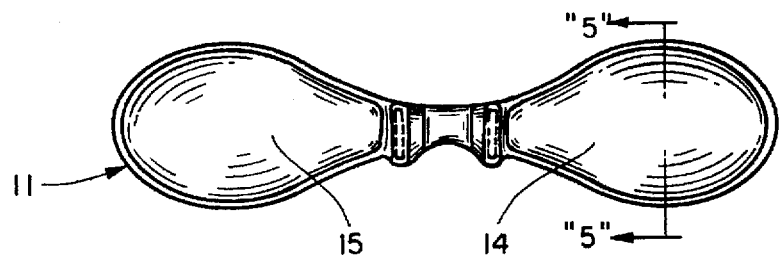
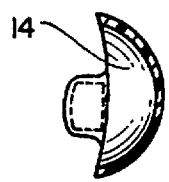
Fig. 4    Fig. 5
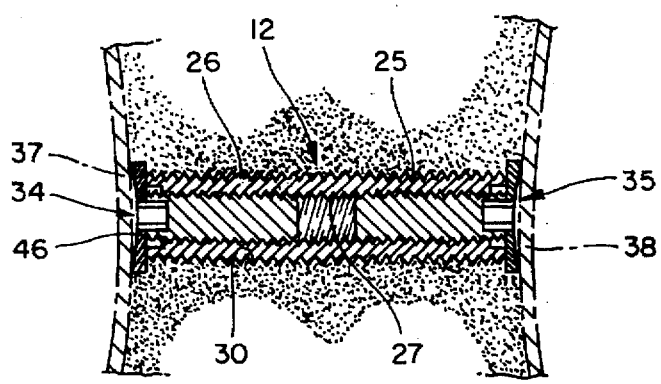
Fig. 6
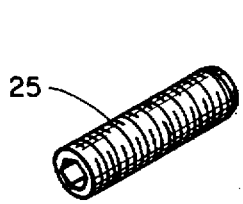
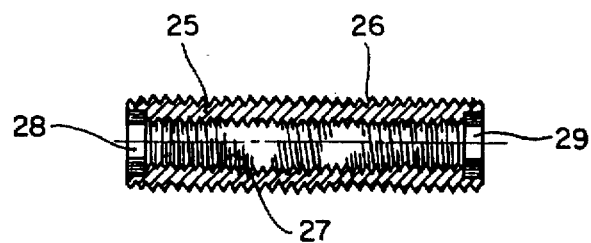
Fig. 7    Fig. 8
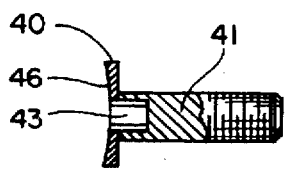
Fig. 9

ETHMOIDAL IMPLANT AND EYEGLASS ASSEMBLY AND ITS METHOD OF LOCATION IN SITU

BACKGROUND OF THE INVENTION

The present method of holding eyeglasses in position about x, y and z axes by an ethmoidal implant is, at the present time, so radical in terms of social acceptance that it is difficult to discuss the prior art as it relates to this new technology. The social departure of this technology from existing eye wear, while in terms of acceptance in the 1990s can be viewed as no more radical than the initial reaction to contact lenses originated by Albert Thicke in about 1887. Mr. Thicke's contact lenses were greeted publicly by the same apprehension as the ethmoidal implant assembly is receiving as of the date of this filing.

Mr. Thicke's contact lenses were constructed of refractive glass, and it was not until about 1938 that plastic contact lenses constructed of methylmethacrylet were developed. Between 1938 to 1950, most contact lenses were made by taking depressions of the eye and forming the lens on the resulting mold. Such lenses covered most of the eye, and a fluid was required under them.

Subsequent to 1950, smaller lenses were developed which covered only the cornea(front surface of the eye) that floated on a layer of tears, and this methodology, of course, eliminated the necessity to make impressions of the curvature of the cornea. The advent of the non-custom molded contact lenses after 1950 revolutionized the social acceptance of contact lenses and proliferated their use to approximately, at the present time, 20% of the refractive corrective ocular patients.

Present day contact lenses are only 7 to 11 mm. in diameter and 0.1 to 1 mm. in thickness and usually can be worn all day without removal. Because contact lenses are invisible and they give a wider field of vision than eyeglasses do, and are not easily broken while participating in active sports, they have represented a significant advance in the art over eyeglasses or spectacles of the rim type that include dual lenses, an interconnecting nosepiece, and rearwardly extending earpieces that assist in orienting the lenses over the eye.

Without overly extolling the virtues of contact lenses, it goes without saying that the vast majority of patients requiring ocular correction are not candidates for the use of contact lenses for a variety of reasons including cornea curvature, natural eye tearing or lack of tearing, infection, irritation and a myriad of other reasons. Thus, there does exist a real need for an ocular correction system that ameliorates at least some of the problems associated with conventional eyeglasses and achieves some of the advantages of contact lenses without their numerous disadvantages.

Applicant conducted a patentability search on this implant assembly and uncovered the following patents:

| INVENTOR | U.S. PAT. NO. | DATE |
| --- | --- | --- |
| Moses | 78,534 | June 2, 1868 |
| Steur, et al. | 5,060,635 | October 29, 1991 |
| Lussi, et al. | 5,167,961 | December 1, 1992 |
| Shetty, et al. | 5,198,308 | March 30, 1993 |
| Heide, et al. | 5,220,918 | June 22, 1993 |
| Vrespa | 5,259,398 | November 9, 1993 |

The Moses, U.S. Pat. No. 78,534 discloses a pair of spectacles having "electrogalvanic battery or batteries" either in the nosepiece or the earpieces of spectacles that cooperate with cutaneous perspiration to create an electric current "to the nerves of the head and obtain the therapeutic effects thereof".

The Steur, et al., U.S. Pat. No. 5,060,635 discloses a ferris rod having titanium nitride coated ends that serve as a fixation assembly for portions of the thoracic and lumbar spine.

The Lussi, et al., U.S. Pat. No. 5,167,961 discloses a synthetic bone material.

The Shetty, et al., U.S. Pat. No. 5,198,308 discloses an orthopedic implant including both a cobalt-based alloy substrate and a titanium fiber metal pad bonded thereto with an inner layer of cobalt-based alloy that includes nickel.

The Heide, et al., U.S. Pat. No. 5,220,918 discloses a magnetic induction hearing aid that utilizes a tympanic rod having a magnet at one end that is positioned in situ in the middle ear.

The Vrespa, U.S. Pat. No. 5,259,398 relates to a cordical implant having varying pitch longitudinal sections to accommodate varying bone mass.

There is, of course, a significant body of art represented in part by the above implants, relating to dental implants utilized to support artificial teeth in the human mouth. The procedures for such implants have some of the present methodology, but in the present art of dental implants it is necessary for the dentist to prepare a "stint" that enables the physician to guide the drill to its desired entry point and to maintain the drill aligned during the drilling process on an axis that such will be consistent with the location of the prosthetic tooth once attached to the implant. However, one of the disadvantages of such stints is that there is frequently stint movement due to the requirement of having the stint supported on tissue in the mouth which inevitably produces movement of the stint relative to the bone to be drilled, and movement of the jaw itself during the procedure has the same effect. Thus, insofar as I am aware, there have been no fixed stints or drill guides developed in the dental field, and thus accurate drilling remains a significant problem in that art.

It is an object of the present invention to provide an ethmoidal implant and eyeglass assembly that provides significant improvement over conventional eye glasses or spectacles and achieves many of the advantages of contact lenses without their incident disadvantages.

SUMMARY OF THE PRESENT INVENTION

In accordance with the present invention, an ocular ethmoidal implant and eyeglass assembly is provided that includes a titanium screw implant adapted to be threaded in situ into the ethmoidal area horizontally and an eyeglass assembly that is magnetically supported and oriented by the implant. Toward this end, the titanium screw has a threaded aperture there-through that receives a pair of subcutaneous magnet assemblies that are threaded by the surgeon into the ends of the screw. The outer surfaces of the magnet are contoured by the surgeon to the proximal ethmoidal surfaces so the entire implant is subcutaneous in the ethmoidal area.

The eyeglasses, according to the preferred embodiment, are relatively small one-piece clear plastic moldings without rims or earpieces having a pair of magnets insert-molded into its nosepiece and positioned to supracutaneously overlie the magnets in the implant assembly. The magnets in the nosepiece are rotationally oriented so that the cooperating magnetic fields properly rotationally position the eyeglasses about a horizontal axis(x), as well as in the vertical x-y plane.

The present ethmoidal implant and eyeglass assembly eliminates the problems associated with the use of contact lenses; namely, infection, irritation, cornea curvature, insertion and removal, and many others.

Because the eyeglasses, according to the present invention, require no earpieces, they can, if desired, be completely rimless and thus, in fact, can be formed of a single or one piece plastic molding of appropriate refractive characteristic. And such glasses are significantly less aesthetically objectionable, at least in the belief of those who prefer but cannot wear contact lenses.

The surgical procedure for implanting the present ethmoidal implant is significantly simpler, more accurate, and less prone to infection than dental implants commonly used today. This is due in part to the fact that the ethmoidal area is significantly less productive for bacterial growth and other infections than the mouth area, but importantly to the fact that the present method of implantation utilizes a fixed drill guide rather than a movable "stint" commonly used in dental implant procedures today.

Other objects and advantages of the present invention will appear more clearly from the following detailed description.

BRIEF DESCRIPTION OF THE DRAWINGS

FIG. 4 is a rear view of the present eyeglass assembly;

FIG. 5 is a cross-section of the eyeglass assembly taken generally along line 5—5 of FIG. 4;

FIG. 6 is a vertical section through the ethmoidal area showing the implant assembly according to the present assembly in situ subcutaneously;

FIG. 7 is a perspective view of the present outer titanium screw in the implant assembly;

FIG. 8 is an enlarged longitudinal section of the outer titanium screw of the implant assembly;

FIG. 9 is a sub-assembly view of one of the magnet assemblies adapted to be threaded into the implant, and;

DETAILED DESCRIPTION OF THE PREFERRED EMBODIMENT

Figure 1:
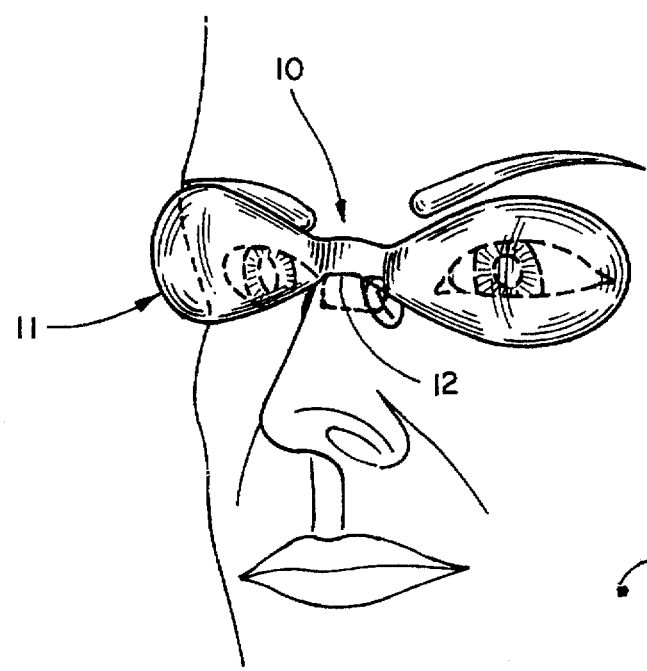
FIG. 1 is a perspective view of the present eyeglass in location on the human face with the ethmoidal implant illustrated in phantom lines.

Referring to the drawings and initially FIGS. 1 to 5, an ocular ethmoidal implant and eyeglass assembly 10 is illustrated according to the present invention consisting of a rimless and earpieceless eyeglass assembly 10 that is essentially a one piece plastic molding, and an ethmoidal implant assembly 12 surgically implanted completely subcutaneously in the ethmoidal bone area proximal to the horizontal axis of the eyes.

The eyeglass assembly 11 is a one piece clear plastic molding with rimless oval lenses 14 and 15 interconnected by an integral nosepiece bridge 16. A pair of integrally formed nosepiece portions 18 and 19 project rearwardly from the nosepiece bridge 16 and have the appropriate curvature for the ethmoidal area.

Figure 2:
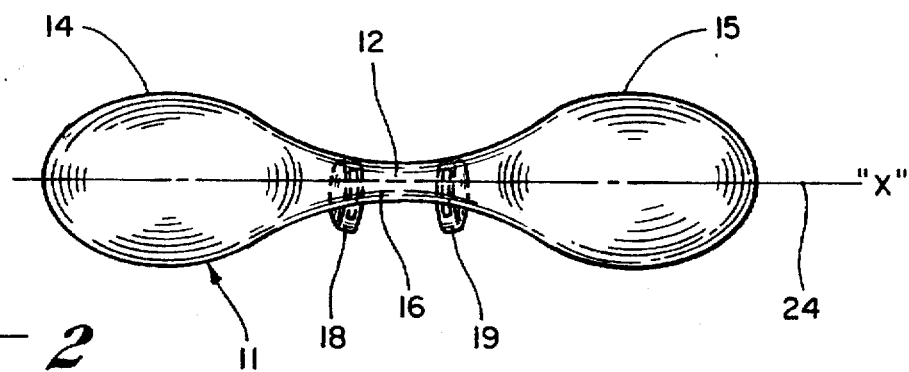
FIG. 2 is a front view of the present eyeglass assembly.
Figure 3:
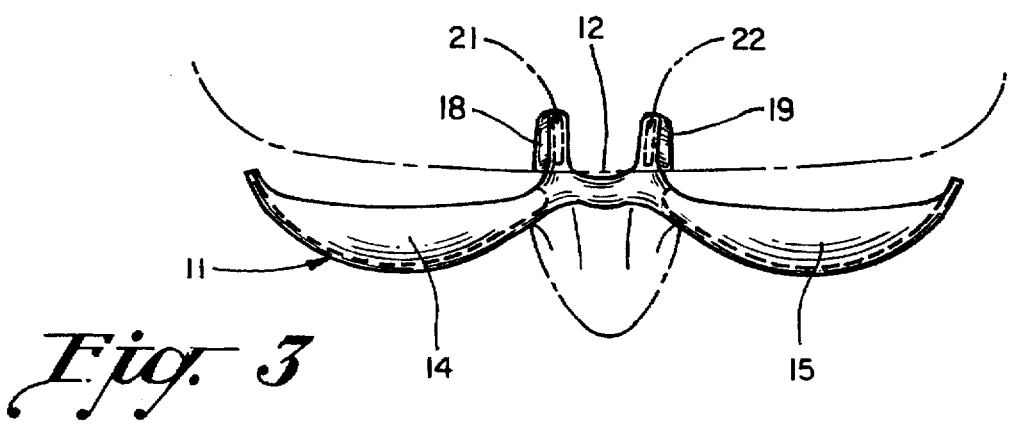
FIG. 3 is a top view of the present eyeglass assembly with the ethmoidal area illustrated in dotted lines.

As seen in dotted lines in FIGS. 2 and 3, a pair of rare earth metal magnets 21 and 22 are insert molded into the nosepiece portions 18 and 19 and have a magnetic field orientation that cooperates with the implant 12 to position the lenses 14 and 15 straight ahead on the appropriate optical axis; i.e., rotationally about axis 24 in FIG. 2.

An important feature is that the eyeglass assembly 11, because of its rimless and earpieceless design, can be made considerably smaller than present day eyeglasses and positioned deeper within the facial eye cavities providing significantly improved aesthetics over present day eyeglasses.

Viewing FIGS. 6 to 9, the ethmoidal implant assembly 12 includes an outer base titanium tube 25 threaded externally at 26 and internally at 27.

As seen more clearly in FIGS. 7 and 8, the ends of the screw 27 have hexagonal sockets 28 and 29 adapted to receive an allen-head wrench for the purpose of threading screw 25 into ethmoidal bone aperture 30. The tool sockets 28 and 29 permit either end of the screw to be initially threaded into the bone and also assist in withdrawing the screw somewhat from the ethmoidal aperture if it is screwed by the surgeon too far in. That is, if socket 28 is used to thread screw 25 into the right side of the ethmoidal (surgeon's left) and is threaded too deeply in aperture 30, the surgeon can insert the wrench in socket 29 and rotate the screw back towards the patient's right until it is appropriately centered.

A pair of identical earth metal magnet assemblies 34 and 35 are threaded into the ends of the screw 25, obviously with skin portions 37 and 38 open and after closure the magnet assemblies are completely subcutaneous.

As seen in FIG. 9, each of the magnet assemblies 34 includes a rare earth magnet 40 bonded to a threaded steel shank 41 with an hexagonal socket 43 projecting through the rare earth magnet 40 into the threaded shank 41. Socket 43 receives an allen-head wrench for threading the magnet assemblies into the screw 25.

While the earth magnet 40 is shown with a concave outer surface 46 in FIGS. 6 and 9, it should be understood that as manufactured, outer surface 46 is flat and is contoured in situ by the surgeon to conform to the patient's ethmoidal proximal contour.

Figure 10:
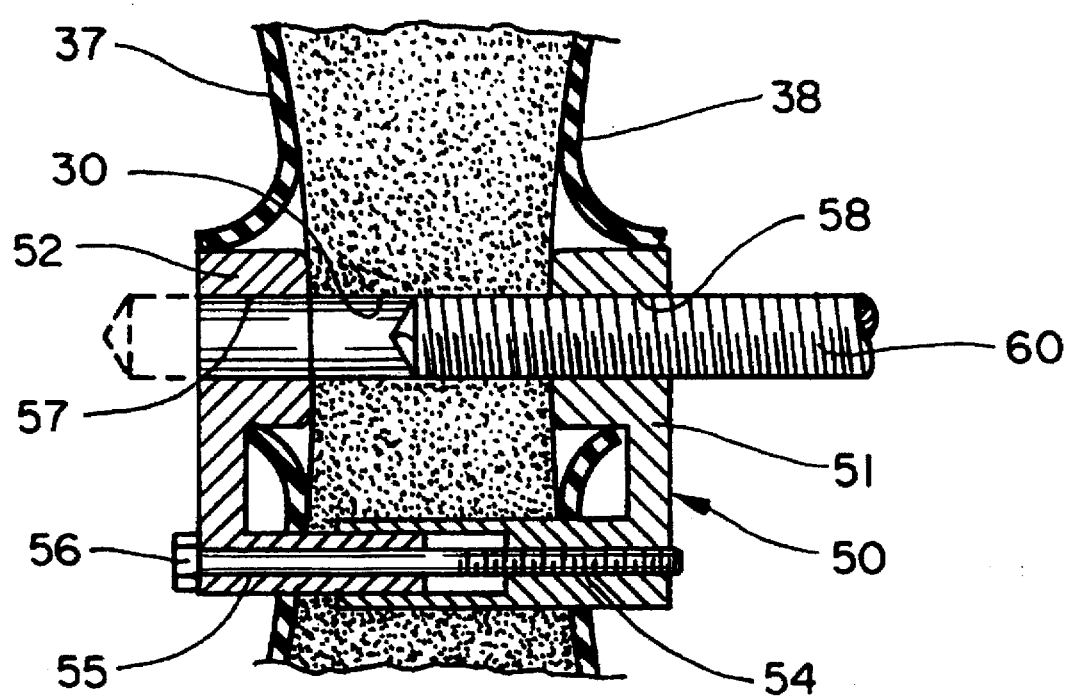
FIG. 10 is another vertical section through the ethmoidal showing the method of drilling the pilot hole for the implant utilizing a fixed dual sided drill guide.

In FIG. 10, a drill guide assembly 50 is illustrated for the purpose of drilling both a pilot hole and a final hole through the ethmoidal bone, and is seen to include a left apertured boss 51 and a right apertured boss 52 interconnected by cross members 54 and 55 that receive a threaded adjustment member 56 for the purpose of controlling the spacing between the apertured bosses 51 and 52. While not shown in the drawings, the apertures 57 and 58 are adapted to receive a plurality of apertured guide bushings to accommodate various diameter drills 60.

An important aspect of the present invention is that the drill guide assembly 50 is fixed to a stationary frame in the surgical area making possible precise drilling of the ethmoidal aperture 30. In the vast majority of surgical procedures, it is not possible to have both entry and exit drill guides fixed to a stationary reference, and of course, this is possible in the ethmoidal case because both sides of the ethmoidal are relatively close to one another and the drill guide can be easily fixed to a stationary frame. Drilling can proceed in one direction or both in the same procedure because either boss 51 or 52 can be the entrance guide.

The magnets 40 in the magnet assemblies are visually marked north and south(N-S) or otherwise coded so that the surgeon can locate the north-south axes opposite to and in alignment with the north-south axes in the eyeglass molded magnets 21 and 22. This appropriately positions the eyeglass assembly 11 rotationally about x axis 24 and, of course, magnets 46 cooperate with magnets 21 and 22 to appropriately position the glass assembly 11 in the x and y plane to the z axis as well.

Because the distance between the nosepiece portions 18 and 19 is fixed and greater than the spacing between magnets 40, and because the strength of the magnets 40 is the same, and the strength of magnets 21, 22 are equal to each other, there is no tendency for the nosepiece portions 18 and 19 to squeeze the nose tissue. This eliminates nosepiece depression in the skin on the sides of the nose and its associated discomfort.

I claim:

1. An ocular ethmoidal implant and eyeglass assembly comprising: an implant adapted to be implanted in situ in the ethmoidal area, connecting means on a portion of the implant, and an eyeglass assembly having a lens portion and a connecting means located in the ethmoidal area to cooperate with the implant connecting means to hold the eyeglass assembly relatively fixed in the ethmoidal area with the lens positioned over the eye.

2. An ocular ethmoidal implant and eyeglass assembly as defined in claim 1, wherein the implant includes a titanium screw adapted to be threaded into the ethmoidal bone.

3. An ocular ethmoidal implant and eyeglass assembly as defined in claim 1, wherein at least one of the implant connecting means and the eyeglass assembly connecting means is a magnet.

4. An ocular ethmoidal implant and eyeglass assembly as defined in claim 3, wherein the outer surface of the implant connecting means is contoured to the proximate surface of the ethmoidal bone.

5. An ocular ethmoidal implant and eyeglass assembly as defined in claim 2, wherein the connecting screw has an aperture therein and the implant connecting means is threaded into the aperture in the titanium screw.

6. An ocular ethmoidal implant and eyeglass assembly as defined in claim 1, wherein the eyeglass assembly includes dual lenses and a connecting nosepiece, said connecting means being located on the nosepiece, said eyeglass assembly being earpieceless.

7. An ocular ethmoidal implant assembly for supporting an eyeglass, comprising: an implant adapted to be implanted in situ in the ethmoidal area, and connecting means on a portion of the implant adapted to hold a cooperating connecting means on the eyeglass, said implant connecting means adapted to cooperate with an eyeglass connecting means to hold the eyeglass relatively fixed in the ethmoidal area.

8. An ocular ethmoidal implant assembly as defined in claim 7, wherein the implant includes a titanium screw.

9. An ocular ethmoidal implant assembly as defined in claim 8, wherein the implant screw has threaded openings in each end, said connecting means including two connectors each having threaded portions threadedly engaged in the openings in the titanium screw.

10. An ocular ethmoidal implant assembly as defined in claim 9, wherein each of the connectors includes a ferromagnetic material.

11. An ocular ethmoidal implant assembly as defined in claim 9, wherein at least one end of the titanium screw has a tool receiving drive socket therein, each of the connectors having a tool receiving drive socket therein.

12. An eyeglass assembly for use with an ethmoidal area implant with connecting means therein, comprising: a lens portion and a connected ethmoidal portion, said ethmoidal portion having connecting means therein adapted to cooperate with the implant connecting means to hold the eyeglass relatively fixed in the ethmoidal area, said eyeglass assembly being earpieceless.

13. An eyeglass assembly as defined in claim 12, wherein said eyeglass includes a pair of lenses and a connecting nosepiece, said nosepiece including said ethmoidal portion, said lenses and nosepiece being a one piece plastic molding whereby the entire eyeglass assembly may be molded in one piece.

14. An eyeglass assembly as defined in claim 12, wherein said eyeglass includes a pair of lenses and a connecting nosepiece, said nosepiece including said ethmoidal portion, said connecting means being a magnet or ferromagnetic material insert molded in the nosepiece.

15. A method of implanting an ocular ethmoidal implant assembly in situ in the ethmoidal area, including the steps of: positioning a drill guide at the ethmoidal area with a drill guide aperture axis perpendicular to the ethmoidal bone extension, fixing the drill guide in position with respect to a stationary reference, drilling an aperture into the ethmoidal bone utilizing the drill guide, inserting an implant into the ethmoidal aperture, and attaching an eyeglass connector to the implant adjacent the proximal ethmoidal surface.

16. A method of implanting an ocular ethmoidal implant assembly as defined in claim 15, wherein the implant has a threaded aperture therein, said step of attaching an eyeglass connector including threading the eyeglass connector into the implant aperture.

* * * * *